US012625391B2

(12) United States Patent
Li

(10) Patent No.: US 12,625,391 B2
(45) Date of Patent: May 12, 2026

(54) WAVEFRONT ENGINEERED LENSES FOR CORRECTION OF PRESBYOPIA AND ASTIGMATISM AND NANOPARTICLE-DOPED LIQUID CRYSTAL STRUCTURES FOR CONTINUOUSLY TUNABLE PHASE MODULATION AND ADAPTIVE LENS

(71) Applicant: Guoqiang Li, Upper Arlington, OH (US)

(72) Inventor: Guoqiang Li, Upper Arlington, OH (US)

( * ) Notice: Subject to any disclaimer, the term of this patent is extended or adjusted under 35 U.S.C. 154(b) by 78 days.

(21) Appl. No.: 16/265,983

(22) Filed: Feb. 1, 2019

(65) Prior Publication Data

US 2020/0249501 A1  Aug. 6, 2020

(51) Int. Cl.
*G02C 7/08* (2006.01)
*A61F 2/16* (2006.01)
*G02C 7/04* (2006.01)
*G02F 1/1335* (2006.01)

(52) U.S. Cl.
CPC ............ *G02C 7/083* (2013.01); *A61F 2/1613* (2013.01); *G02C 7/04* (2013.01); *G02F 1/133504* (2013.01)

(58) Field of Classification Search
CPC .......................... G02F 1/133504; G02C 7/083
See application file for complete search history.

(56) References Cited

U.S. PATENT DOCUMENTS

| | | | | |
|---|---|---|---|---|
| 2005/0271325 A1* | 12/2005 | Anderson | ............... | G02F 1/295 |
| | | | | 385/39 |
| 2006/0227283 A1* | 10/2006 | Ooi | ................... | G02F 1/134363 |
| | | | | 349/201 |
| 2010/0195008 A1* | 8/2010 | Hegmann | .............. | C09K 19/56 |
| | | | | 977/773 |
| 2010/0225834 A1* | 9/2010 | Li | .................... | G02F 1/133526 |
| | | | | 349/13 |

FOREIGN PATENT DOCUMENTS

| | | | | | |
|---|---|---|---|---|---|
| CN | 105572946 A | * | 5/2016 | | |
| CN | 108205208 A | * | 6/2018 | .......... | A61F 2/1451 |
| JP | 2005189434 A | * | 7/2005 | ........ | G02F 1/13306 |
| JP | 2009294653 A | * | 12/2009 | | |
| KR | 20080001141 A | * | 1/2008 | | |

OTHER PUBLICATIONS

English translation of KR 20080001141 A (Year: 2008).*
English translation of JP 2009237226 A (Year: 2009).*
CN-105572946-A English translation (Year: 2016).*
JP-2005189434-A English translation (Year: 2005).*

* cited by examiner

*Primary Examiner* — Charlie Y Peng

(57) ABSTRACT

In some embodiments, wavefront engineered contact/scleral/intraocular lenses correct presbyopia and/or astigmatism. Some aspects relate to apparatuses including structures doped with certain nanoparticles to enhance alignment of liquid crystal materials. Some embodiments relate to tunable optical lenses for vision correction that have a structure with doped nanoparticles in the liquid crystal layer and alignment layer or only with blue phase liquid crystal layer without any alignment layer.

6 Claims, 14 Drawing Sheets substrate
electrode
Nanopartic-doped
Alignment layer
electrode
substrate

Nanoparticle-doped
liquid crystal driver

Diffractive/
Fresnel
lens substrate
electrode
alignment
layer
electrode
substrate Nanoparticle-doped
liquid crystal driver Diffractive/
Fresnel
lens

WAVEFRONT ENGINEERED LENSES FOR CORRECTION OF PRESBYOPIA AND ASTIGMATISM AND NANOPARTICLE-DOPED LIQUID CRYSTAL STRUCTURES FOR CONTINUOUSLY TUNABLE PHASE MODULATION AND ADAPTIVE LENS

STATEMENT REGARDING FEDERALLY SPONSORED RESEARCH

This invention was made partially with government support (liquid crystal devices part) under Grant no. R01 EY020641 awarded by the National Institutes of Health. The government has certain rights in the invention.

CROSS-REFERENCE TO RELATED APPLICATIONS

This application contains the intellectual properties described in provisional patent No. 62/624,962 and provisional patent #62624929, both submitted to USPTO on Feb. 1, 2018.

BACKGROUND

A natural phenomenon of the human eye as it ages is the loss of accommodation by the crystalline lens. At childhood, the accommodative ability of the eye can be well above 10 diopters (D), but this figure drops almost linearly to 1 D by the age of 50-60. Almost everyone starts to have difficulty in near-vision tasks at 40-45 years of age. This condition, termed presbyopia, is increasingly important in the US due to the lengthening of life expectancy. Right now about 123 million American adults are presbyopic, and 2 billion worldwide. The number of cases will keep increasing. To care for the vision of such a large population is of great value.

Many techniques are used to correct presbyopia,[1-6] including nonsurgical (spectacles and contact lenses) and surgical (conductive keratoplasty, excimer laser techniques, multifocal intraocular lens (IOL), and corneal inlays). For spectacle lenses, the solutions include bifocal, trifocal, and progressive addition lenses. They are all based on the area-division concept, i.e., each area of the spectacle lens has a different focusing power corresponding to near, intermediate, and distance vision. Consequently, the field of view and head and eye positions are limited for each vision task. An alternative method is monovision, where one eye is corrected for distance vision and the other eye is corrected for near vision. The disadvantages include the loss of stereopsis, the adaptation of the brain in information processing, and night driving.

The electro-optic adaptive lens can overcome these shortcomings, and it is still an active research topic.[7-26] According to the Vision Council of America, approximately 75% of adults use some sort of vision correction, and about 11% of them wear contact lenses.[27] Data suggests the majority of contact lens wearers prefer to stay in contacts once they become presbyopes; most contact lens wearers, 91% of the 35-55 year olds, would like to continue wearing their lenses when they become presbyopic[28]. Disposable lenses are a good choice for presbyopes who would like to occasionally wear contact lenses. Current contact lens options include[29-34] (1) distance-vision contact lenses worn in combination with reading glasses; (2) monovision; (3) bifocal soft and rigid gas-permeable contact lenses; and (4) aspheric multifocal soft and rigid gas-permeable contact lenses. All of these solutions suffer from the same disadvantages listed above. Multifocal contact lenses also reduce contrast because the in-focus and out-of-focus images overlap with each other. The electro-optic adaptive lens, which changes power across the whole aperture, does not fit the contact lens format. There are no existing solutions for contact lenses that enable natural and binocular vision. This gap offers a great opportunity for making a very significant contribution to improve vision for millions of people.

One approach to address these issues is to create an extended depth of field (EDoF) for the human eye with an optical aid. Depth of field (DoF) is the range in the object space within which an acceptable image can be obtained at the fovea. Theoretically, the DoF of a lens or an optical system is proportional to the square of the f/#, where $f/\# = f/D$ with f and D being the effective focal length and the effective aperture of the lens or of the system. The DoF can be extended by limiting the effective aperture of the eye and sacrificing the light and field of view. It would be optimal if the DoF could cover near, intermediate, and distant objects. Recently there have been reports on implantation of a small-aperture corneal inlay to treat presbyopia after laser in situ keratomileusis (LASIK) surgery.[6] This procedure improves near vision with a minimal effect on distance vision and results in less dependence on reading glasses. However, due to the small aperture (e.g., the latest model ACI 7000PDT of the Kamra inlay has a 3.8-mm outer diameter and a 1.6-mm central aperture), the pupil is at least partially occluded across large areas of the field of view, including the central vision. This results in an interocular difference in retinal illumination.[6]

Other amplitude apodization methods[35-36] have been proposed for EDoF, but amplitude modulation inherently reduces light throughput. Another approach that produces an EDoF is to induce spherical aberration of the eye or the eyewear. However the DoF can be improved by only a few percent by inducing spherical aberration.[37] The imaging quality can be more dependent on the movement of the eye. A clinical study by Bakaraju et al.[38-41] compared EDoF contact lenses and two commercial multifocals (Acuvue Oasys for presbyopia, Johnson & Johnson and Air Optix Aqua Multifocal, Alcon). All three of these contact lenses induce high-order spherical aberrations for EDoF, but with different distributions and amplitudes. The spherical aberration profiles are shown in FIG. 1 of Ref. 40. The best near-vision visual acuity achieved was about 20/50 or 0.4 log MAR. Two other studies' reported the use of binary annular concentric phase masks for spectacle lenses and contact lenses to extend of the DoF. However, the experimental results with the spectacle lenses (FIGS. 2 and 8 in Ref 42) do not reflect much success. Better approaches are needed for improved visual acuity and light efficiency.

It is with respect to these and other considerations that the various embodiments described below are presented. Among other aspects of the present disclosure as will be described in further detail herein, the inventor has recognized that it can be more efficient if a pure phase component may be added to the cornea or the contact lens and the DoF enhanced for correction of presbyopia with high light efficiency, large field of view, high contrast sensitivity, and retention of binocular vision.

As known in the art, when voltage is applied to a liquid crystal (LC) cell, the orientation of the molecules of the liquid crystal cell can be changed for continuous phase modulation. Liquid crystals are currently used in a variety of areas in optical applications, including display screens and for corrective vision implementations such as liquid crystal-based lenses for correcting vision problems (e.g., near, intermediate, or distance vision problems). Liquid crystal lenses can be constructed for spectacle, contact lens, and intraocular lens.

Conductive layers (e.g. electrodes) can be coupled to the liquid crystal cell structure, such that an applied voltage causes a change in the orientation of the liquid crystal molecules and thereby a change in optical properties in an apparatus having these various components. Current approaches to tunable liquid crystal lens structures can require, for successful and desired alignment in the liquid crystal cell, two or more alignment layers to be used, for example an alignment layer at a top of the liquid crystal cell portion and an alignment layer at the bottom of the liquid crystal cell.

It is with respect to these and other considerations that the various embodiments described below are presented.

SUMMARY

In some aspects, the present disclosure relates to wavefront engineered contact/scleral lenses for correction of presbyopia and astigmatism. In accordance with some embodiments, optimized phase functions are used to design, fabricate, and test individualized wavefront engineered contact/scleral lenses to correct presbyopia. Implementations of certain aspects and embodiments achieve much better visual performance than aspheric/spherical aberration added contact lenses. 20/20 vision may be produced across a DoF range from 25 cm to infinity with similar imaging quality on the retina. In contrast to the binary phase function, other phase functions are used, including cubic and general cubic phase profiles. Further, new merit functions are defined, and the wavefront profile can be optimized by considering the consistency of the modulation transfer function (MTF) for different object distances, different fields at each object distance, and at different wavelengths across the visible spectrum. The effect of pupil size and displacement is analyzed. Comparisons are presented herein of lenses in accordance with embodiments of the present disclosure with normal contact lenses and lenses based on spherical aberrations.

Individualized wavefront engineered lenses in accordance with some embodiments of the present disclosure can also simultaneously correct astigmatism, the displacement of focal spots formed by the tangential and sagittal ray fans. For regular astigmatism of the eye, these two planes are orthogonal, and is correctable by contact lenses with cylindrical power. Some people have irregular astigmatism caused by two meridians that are not orthogonal, frequently due to keratoconus or refractive surgery. Irregular astigmatism cannot be corrected with spectacles or soft contact lenses. A scleral lens in accordance with some embodiments can correct the corneal astigmatism due to the index-matched tears filling in between the sclera lens and the cornea. Because the DoF is extended to 4 D, regular or irregular astigmatism less than 4 D may be corrected.

Among other benefits and advantages provided, embodiments of the present disclosure described herein provide our aging society with new and powerful solutions to a long lasting and challenging vision problem. Lenses in accordance with some embodiments provide for customized correction of presbyopia and regular and irregular astigmatism. Individualized and custom design, fabrication, and testing can be performed for various presbyopic patients without astigmatism and with regular astigmatism of less than 4 D.

Other aspects and features according to the present disclosure will become apparent to those of ordinary skill in the art, upon reviewing the following detailed description in conjunction with the accompanying figures.

In one aspect, the present disclosure relates to an apparatus for correction of vision of a subject. In one embodiment, the apparatus includes a liquid crystal layer. The apparatus also includes a single alignment layer coupled to the liquid crystal layer and doped with nanoparticles for enhancing alignment of liquid crystal materials in the liquid crystal layer. The liquid crystal layer is doped with nanoparticles for enhancing alignment of the liquid crystal materials. The apparatus also includes a lens portion coupled to the liquid crystal layer and configured such that, when a voltage is applied across the liquid crystal layer, one or more optical properties of the apparatus are changed to provide correction of vision for a subject.

These and other aspects and features in accordance with embodiments of the present disclosure will be apparent from the following description and the accompanying drawings.

BRIEF DESCRIPTION OF THE DRAWINGS

Reference will now be made to the accompanying drawings, which are not necessarily drawn to scale.

DETAILED DESCRIPTION

Figure 1:
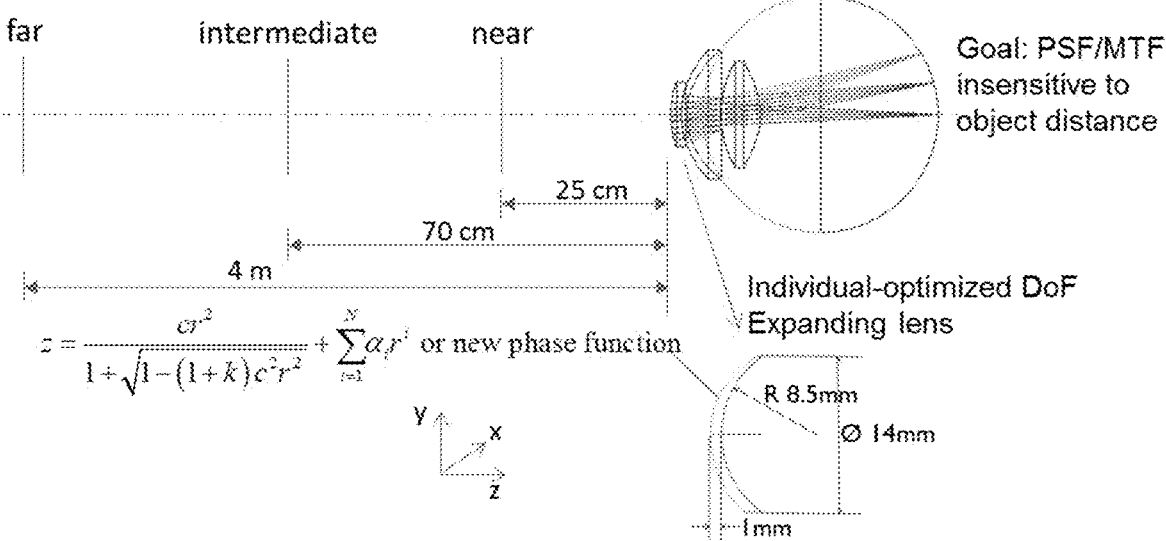
FIG. 1 illustrates a wavefront engineered lens for correction of presbyopia.
Figure 2:
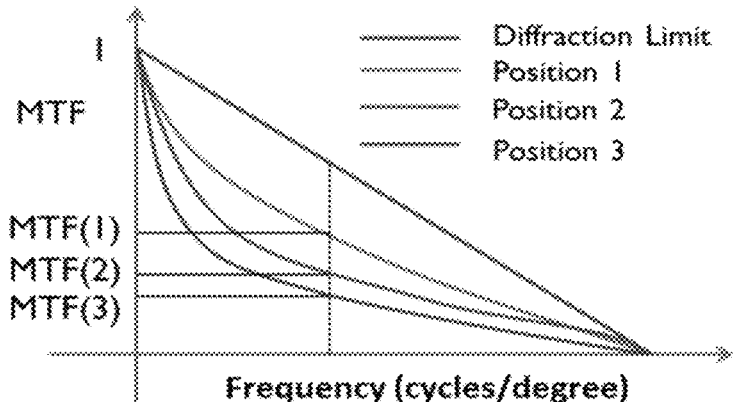
FIG. 2 illustrates the MTF for different object positions, including different object distances (configurations) and different fields at the same object distance.

Some aspects of the present disclosure relate to individualized wavefront engineered contact/scleral lenses for correction of presbyopia and regular and irregular astigmatism. Although example embodiments of the present disclosure are explained in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value. As used herein, "about" means within 20 percent or closer of a given value or range.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

As used herein, a "scleral lens" refers to a lens that rests on the sclera and creates a tear-filled vault over the cornea. A scleral lens and is generally larger than a standard contact lens. A scleral lens is formed as a rigid gas permissible lens, and it can be more stable on the eye (less movement) than standard contact lenses.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

Some references, which may include patents, patent applications, and various publications, are cited in a reference list and discussed in the disclosure provided herein. The citation and/or discussion of such references is provided merely to clarify the description of the present disclosure and is not an admission that any such reference is "prior art" to any aspects of the present disclosure described herein. All references cited and discussed in this specification are incorporated herein by reference in their entireties and to the same extent as if each reference was individually incorporated by reference.

The following description provides a further discussion of certain aspects of the present disclosure in accordance with example embodiments. The discussion of some example implementations also refers to corresponding results which includes experimental data. Experimental data presented herein is intended for the purposes of illustration and should not be construed as limiting the scope of the present disclosure in any way or excluding any alternative or additional embodiments.

In some aspects, the present disclosure relates to individualized wavefront engineered contact/scleral lenses for correction of presbyopia and regular and irregular astigmatism with 20/20 vision from far to near vision tasks. Optimization approaches and phase functions in accordance with various embodiments presented herein provide extension of the DoF of the human eye. Among other innovations, various embodiments of the present disclosure take the aberrations of the whole eye into account for design and optimization of the wavefront profiles. Further, different phase functions are analyzed, including cubic, general cubic, general polynomial, and rotationally symmetric, among others, for extension of DoF of the human eye. Such phase functions are very different from the spherical aberration terms. Additionally, various embodiments of the present disclosure can reduce the effects of relative movement between the scleral lens and the eye by analyzing the symmetric phase profile. Innovative merit functions developed for optimization of the phase functions are also presented, so that 20/20 vision can be achieved and maintained for object distances from 25 cm to infinity. An objective of the optimization is to maintain the consistency of the MTF for different object distances, different fields of view of each object distance, and different wavelengths, and for both sagittal and tangential rays. Further, displacement of the contact/scleral lenses in accordance with various embodiments are optimized with respect to the eye and the pupil size. In some implementations, the embodiments can correct any astigmatism less than 4 D. As will be shown, visual performance can be almost the same for near, intermediate, and distance vision. Results presented show that various embodiments of the present disclosure can outperform contact lenses that use higher-order spherical aberration terms and designs using binary phase functions.

The following provides a further discussion of concepts and background for understanding wavefront engineered contact/scleral lenses for the correction of presbyopia and astigmatism in accordance with some embodiments of the present disclosure. Of note, imaging with a microscope differs from human vision in that for microscope imaging, the images are received by a camera interfaced with a computer that digitally encodes the image, and in contrast, for human vision, the images are formed at the retina and sent to the brain without digital decoding.

When there is no digital decoding involved for vision correction, it is more challenging to design a wavefront engineered contact/scleral lens. It is of high importance to select the right type of phase function and define the right procedure for optimizing the coefficients of the phase terms. For example, for correction of presbyopia, an ultimate goal can be to have 20/20 to 20/25 vision at the retina for a large range of object distances from 25 cm to infinity by superimposing the phase function onto the contact/scleral lens.

Now also referring to optics geometry and the wavefront engineered contact/scleral lens illustrated in FIG. 1, in space domain, imaging quality is characterized by the point spread function (PSF). Correspondingly, in the frequency domain, it is characterized by the modulation transfer function (MTF), which is the amplitude of the optical transfer function. To generate an effective DoF for the eye spanning from 25 cm to infinity (e.g., 4 m), the contact/scleral lens is designed so that the PSF is insensitive to the object distance within the range of the DoF. This can be achieved by engineering the phase function at the front surface of the contact lens. The total phase profile of this surface can be expressed by $$z = \frac{cr^2}{1 + \sqrt{1 - (1 + k)c^2 r^2}} + \sum_{i=1}^{N} \alpha_i r^i + \text{wavefront coding}, \tag{1}$$

where c is the curvature, k is the conic coefficient, r is the radial coordinate with $r^2 = x^2 + y^2$, and the $\alpha$ terms aspheric coefficients, which can be used to correct aberrations. Innovative approaches in the design, in accordance with various embodiments of the present disclosure, include new merit functions and analyzing different wavefront functions that have not been studied for vision correction.

Merit Functions for Optimization

In accordance with some aspects of the present disclosure, merit functions and wavefront functions can be written and added to optical design software to perform the optimization, for example Zemax[45] software. The optimization contains two parts: one is the merit function, which can be treated as the "target" of the optimization; the other is the optimization method, which is the way to find the target. In Zemax, the default merit function is the root mean square (RMS) of the spot in the image plane. For a conventional optical system, it should be as small as possible to achieve a sharp image for a fixed object plane. However, for the design of the add phase function for extending the DoF of the human eye, the MTF must be kept to be good for all object distances, all fields at each object distance, and all wavelengths within the desired DoF so that acceptable images can be obtained at the retina for the entire DoF. Accordingly, new merit functions are developed, in accordance with some embodiments of the present disclosure, based on the consistency of the MTF at different positions and different wavelengths for optimization.

Different positions come from different object distances (configurations) and different fields at the same object distance. The standard deviation of the MTF at certain frequencies can be used to represent the consistency of the MTF and define it as the merit function E:

$$E = \frac{\sum_{j=1}^{N_v} \sum_{i=1}^{N_u} w(i,j) \sqrt{\sum_{n=1}^{N_F} \sum_{m=1}^{N_o} [MTF(D_o(m), F(n), u(i), v(j)) - \overline{MTF}(u(i), v(j))]^2}}{N_F N_o \sum_{j=1}^{N_v} \sum_{i=1}^{N_u} w(i,j)}, \qquad (2)$$

where $D_o(m)$ is the object distance at the $m^{th}$ configuration and $N_o$ is the total number of configurations; $F(n)$ is the $n^{th}$ field and $N_F$ is the total number of fields; $u(i)$ and $v(j)$ are frequencies at the $i^{th}$ and the $j^{th}$ positions respectively; $w(i,j)$ is the weight at the frequencies $u(i)$ and $v(j)$; $MTF(\cdot)$ represents the MTF value; $N_u$ and $N_v$ are the number of frequencies $u(i)$ and $v(j)$ respectively. The average value of the MTF, $\overline{MTF}(u(i), v(j))$, is described as $$\overline{MTF}(u(i), v(j)) = \frac{1}{N_F N_o} \sum_{n=1}^{N_F} \sum_{m=1}^{N_o} MTF(D_o(m), F(n), u(i), v(j)). \qquad (3)$$

In practical design, all frequencies up to 100 cycles/degree are considered. The more frequencies involved, the more time it takes and the more accurate results can be obtained. To make the MTF curves at different object distances and different fields be consistent with each other, the merit function in Eq. (2) should be as small as possible. However, the MTF values will be reduced to zero if no penalty factors are taken into consideration. For this reason, a threshold method is used as a penalty factor, Eq. (4).

$$P(m,n) = \begin{cases} P_0 & \min_{i,j} MTF(D_o(m), F(n), u(i), v(j)) \le T \\ 0 & \text{otherwise} \end{cases}, \qquad (4)$$

where T is the threshold of the MTF; and $P_0$ is a large constant defined by user. $w_p$ is the weight of the penalty factor. Then the modified merit function can be represented as $$E' = E + w_p \sum_{n}^{N_F} \sum_{m}^{N_o} P(m,n). \qquad (5)$$

The above merit function is general, i.e., it can be used for both symmetric and asymmetric phase functions. If the add phase function is symmetric, default merit function can be modified for the design of the symmetric optical system.

Phase Functions and Comparison of Optical Quality

In the past, the binary phase function has been considered for vision correction. It has the following format:

$$z(x, y) = \begin{cases} 0, & r < r_1 \text{ or } r_2 < r < r_0; \\ \pi, & r_1 \le r \le r_2. \end{cases} \qquad (6)$$

In accordance with embodiments of the present disclosure, merit functions have been developed to optimize the parameters for correction of presbyopia. The inventor has found that the binary phase plates can extend DoF in contact lenses, but the visual acuity is low in comparison with the other phase functions listed below.[44, 46-47]

Cubic phase function: $z(x,y) = a(x^3 + y^3)$. $\qquad (7)$

Figure 3:
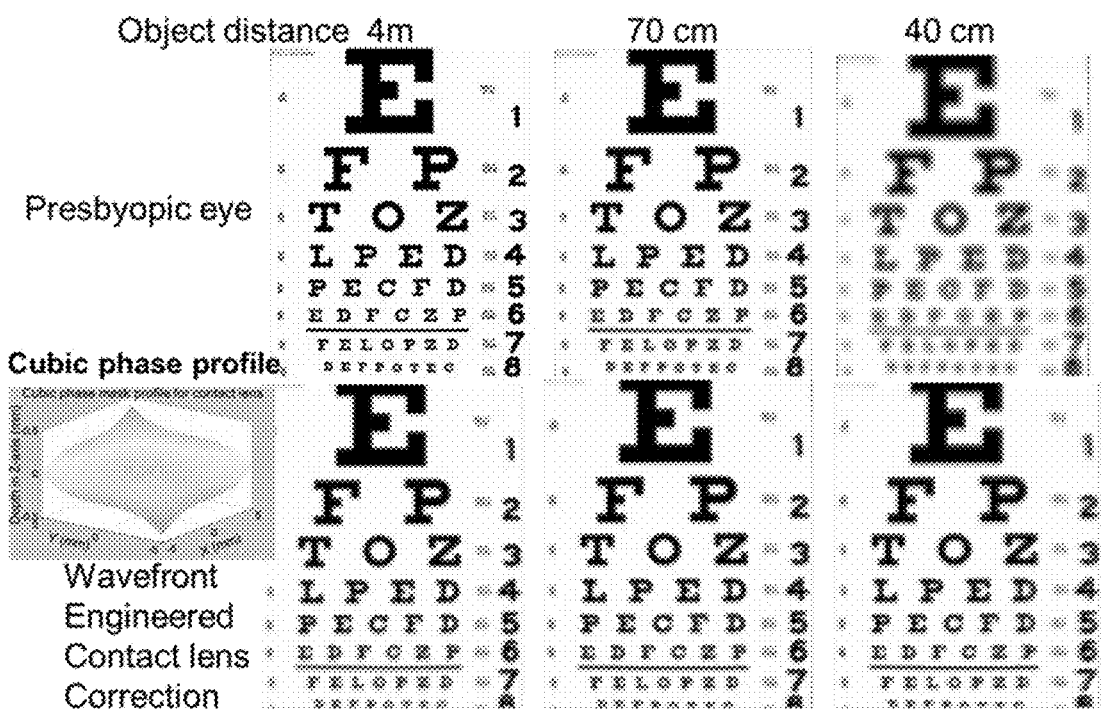
FIG. 3 shows a comparison of visual acuity at distance (4 m), intermediate (70 cm), and near (40 cm) vision, where the upper row is for the emmetropic eye with presbyopia, and the lower row is for a cubic phase wavefront-coded emmetropic eye.

General cubic phase function: $z(x,y) = a(x^3 + y^3) + b(x^2 y + x y^2)$. $\qquad (8)$ Feasibility Study Two new approaches were used to demonstrate the feasibility of new functions to correct presbyopia in accordance with various embodiments of the present disclosure. Sagittal and tangential MTF values were taken into consideration in the optimization. For example, FIGS. 3-5 demonstrate the feasibility of using a wavefront-coded phase plate to correct presbyopia. FIG. 3 is the image result at the retina using the cubic phase function. The emmetropic eye model was provided in Zemax, and the above optimization method was used to calculate the coefficient of the cubic phase with the result a=0.00163 in Eq. (7). The profile is shown in the left side of FIG. 3. Note that the phase profiles used are very different from those in FIG. 1 of Ref 40 for higher-order spherical terms. The method can be extended to any hyperopic and myopic eye. In reality, the pupil size is affected by illuminance, age, monocular/binocular vision, and field size.[48] In general, with dim light (scotopic vision), the pupil size is larger, but with aging and binocular vision, the pupil is smaller. For aging eyes, a realistic pupil size of 3 mm was used for simulation. In FIG. 3, the upper row shows the images on the retina of an emmetropic eye for distance (4 m), intermediate (70 cm), and near (40 cm) vision. The lower row shows the images by adding a cubic phase plate for correction of presbyopia. The bottom line corresponds to 20/20 vision. For the emmetropic eye with presbyopia, the image for near vision is greatly blurred. In contrast, using the wavefront coding technique, all of the images through the large DoF are almost the same, verifying the capability of offering 20/20 vision for all vision tasks.

Additional Developments

Among other further aspects in accordance with embodiments of the present disclosure, a general polynomial function (Eq. 9) can be used:

$$\text{General polynomial function: } z(x, y) = \sum_{n=2}^{k} \sum_{m=0}^{n} C_{m(n-m)} x^m y^{n-m}, \quad (9)$$

where m,n are positive integers; and k is the highest power of x, y. Considering the computation efficiency, k=5 is used for some implementations described herein.

Figure 4A:
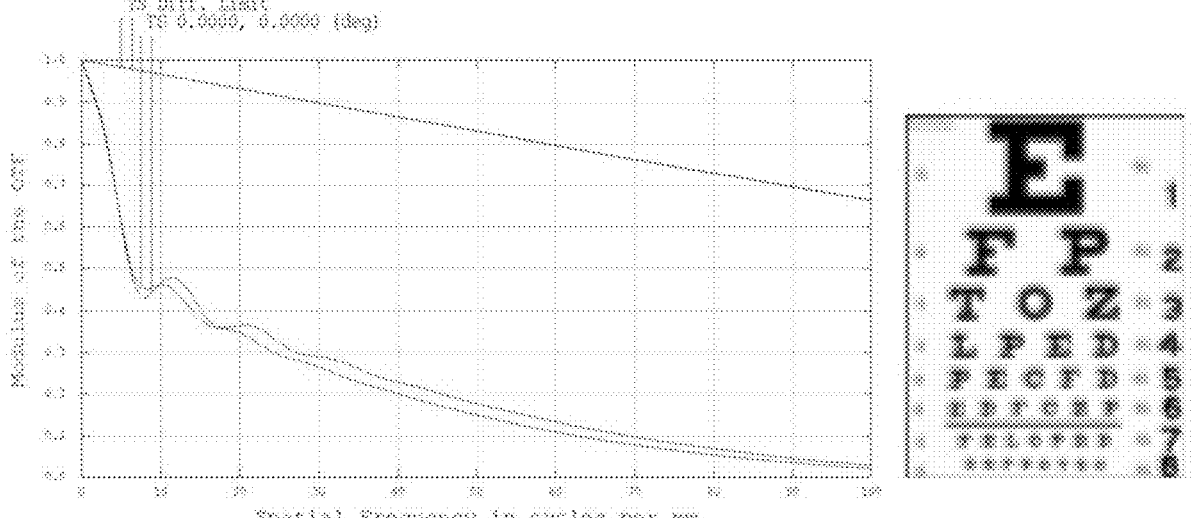
FIGS. 4A-4C show MTF curves and images at the retina for the emmetropic eye with presbyopia at object distances of 4 m (FIG. 4A), 70 cm (FIG. 4B), and 40 cm (FIG. 4C).
Figure 4B:
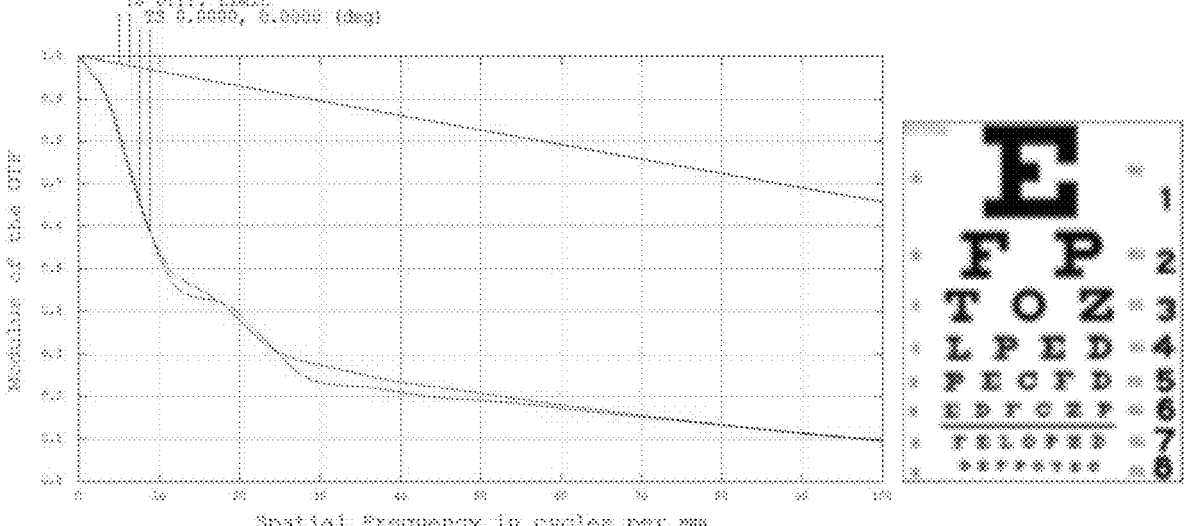
Figure 4C:
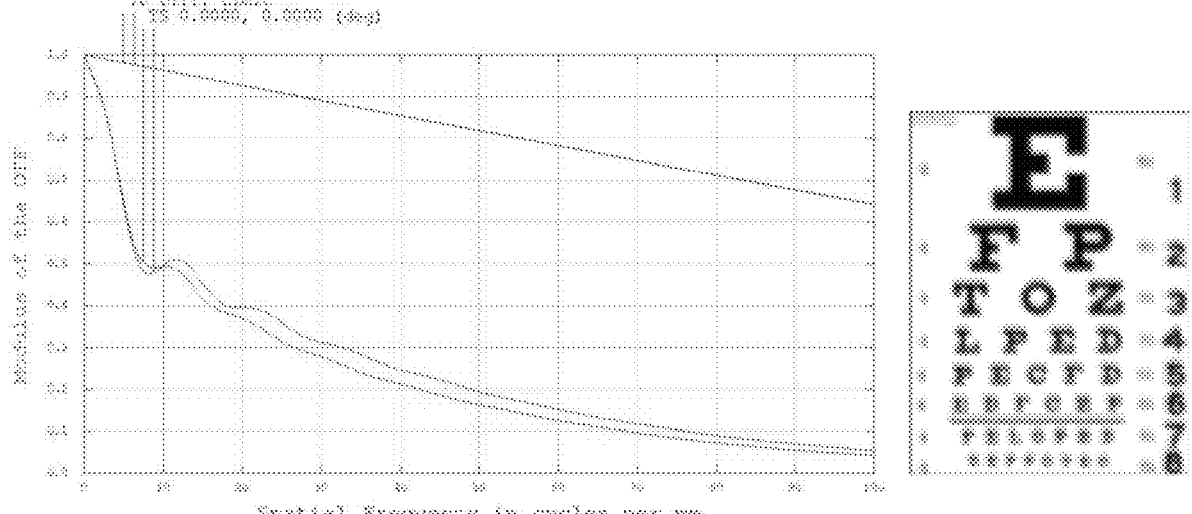
Figure 5A:
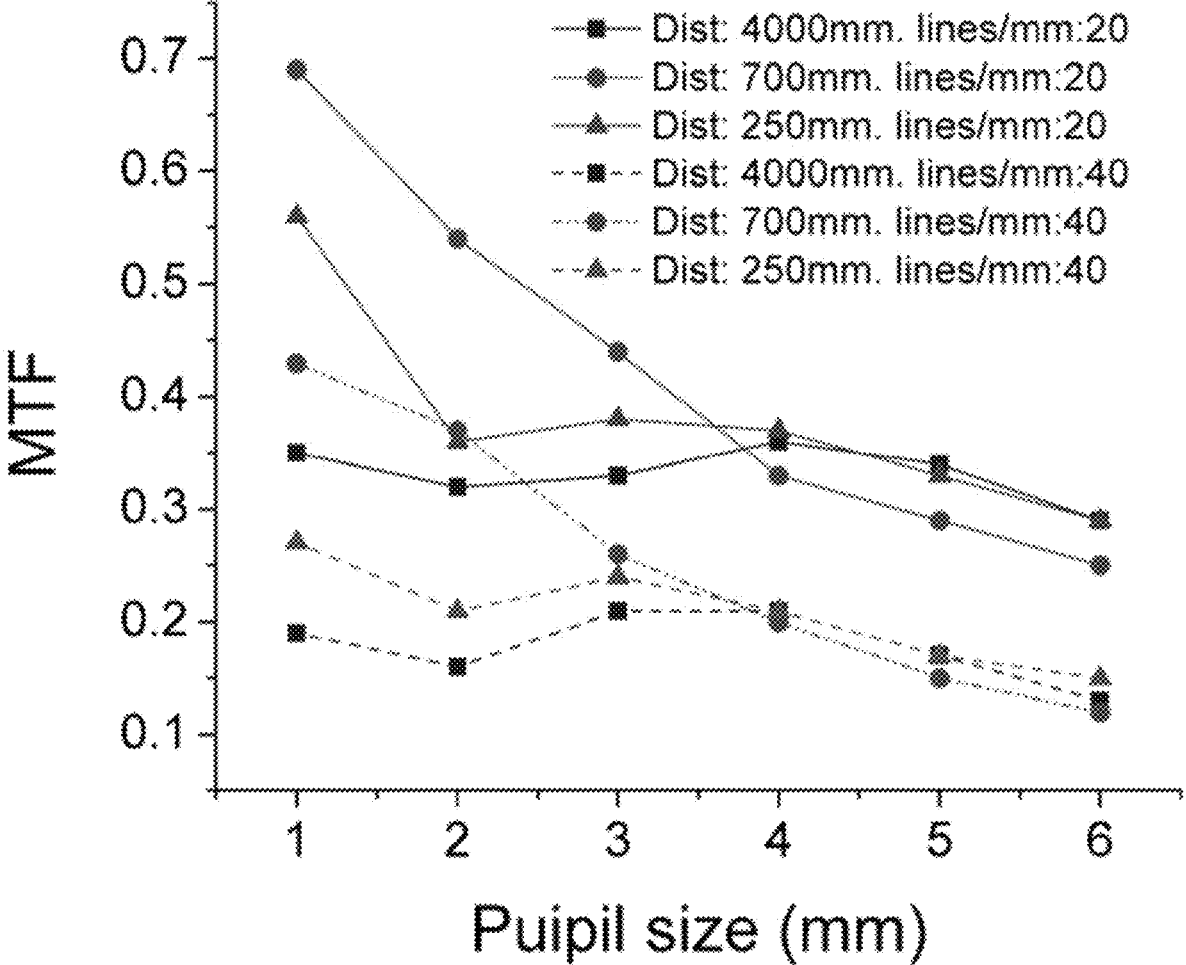
FIGS. 5A-5D show effects of pupil size and displacement of the contact lens with respect to the eye, where the results are based on a design from the application of the general polynomial phase function.
Figure 5B:
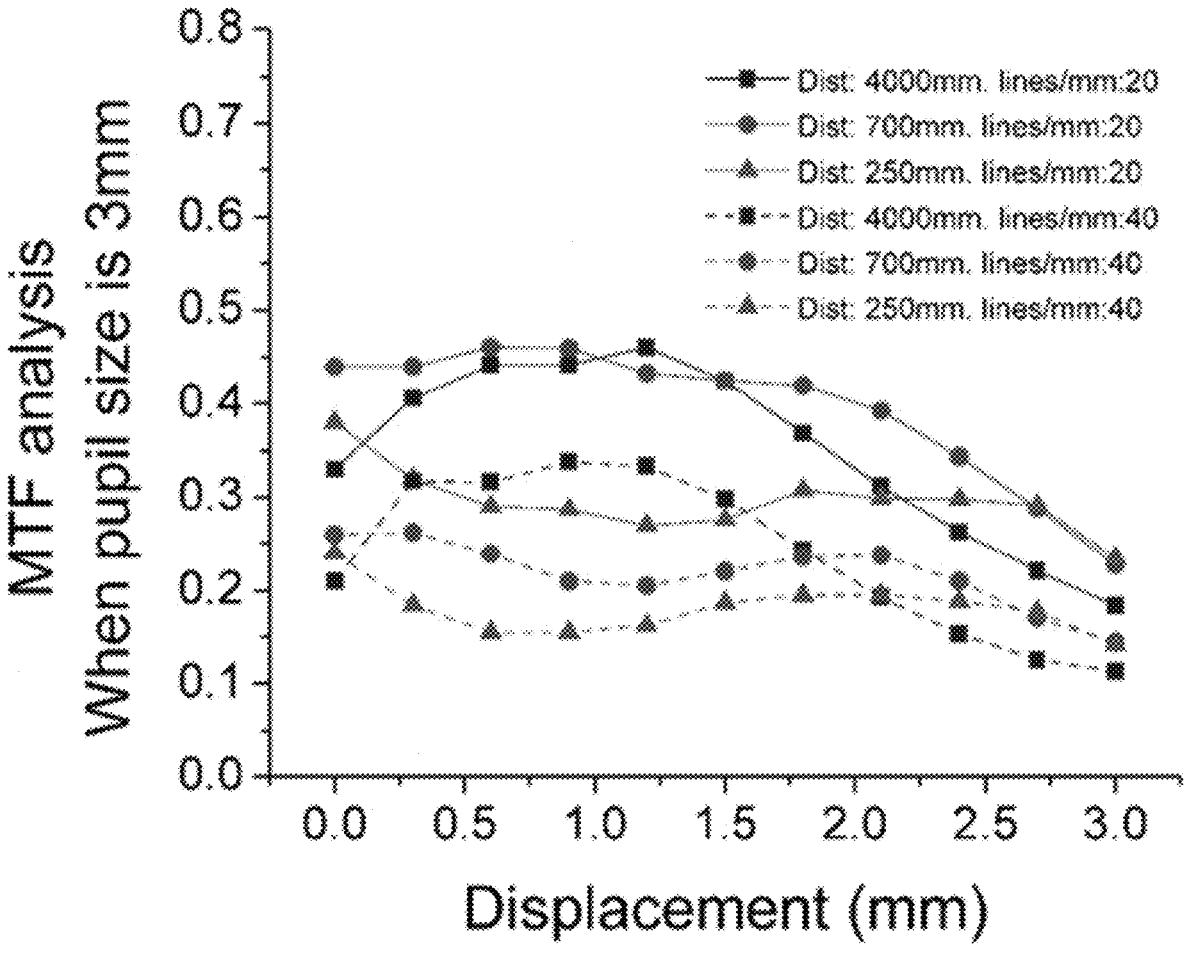
Figure 5C:
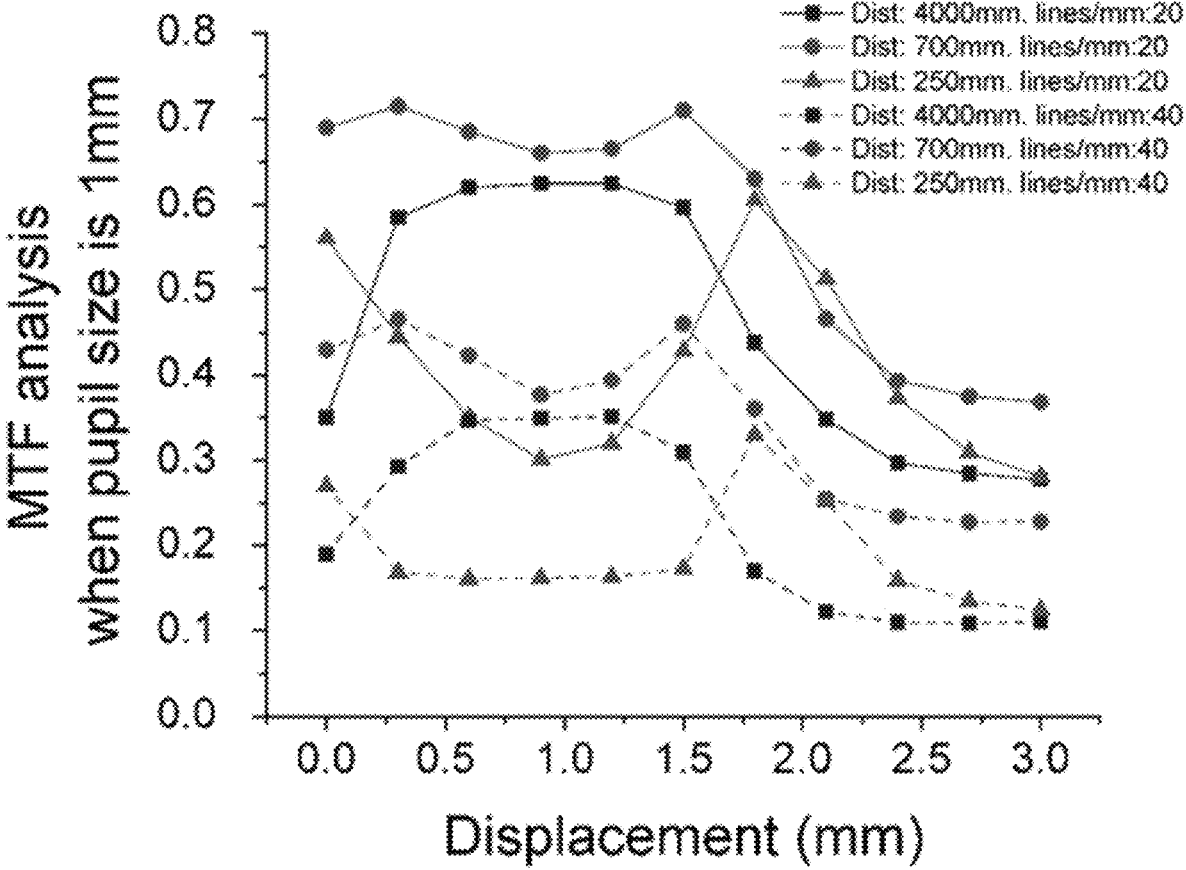
Figure 5D:
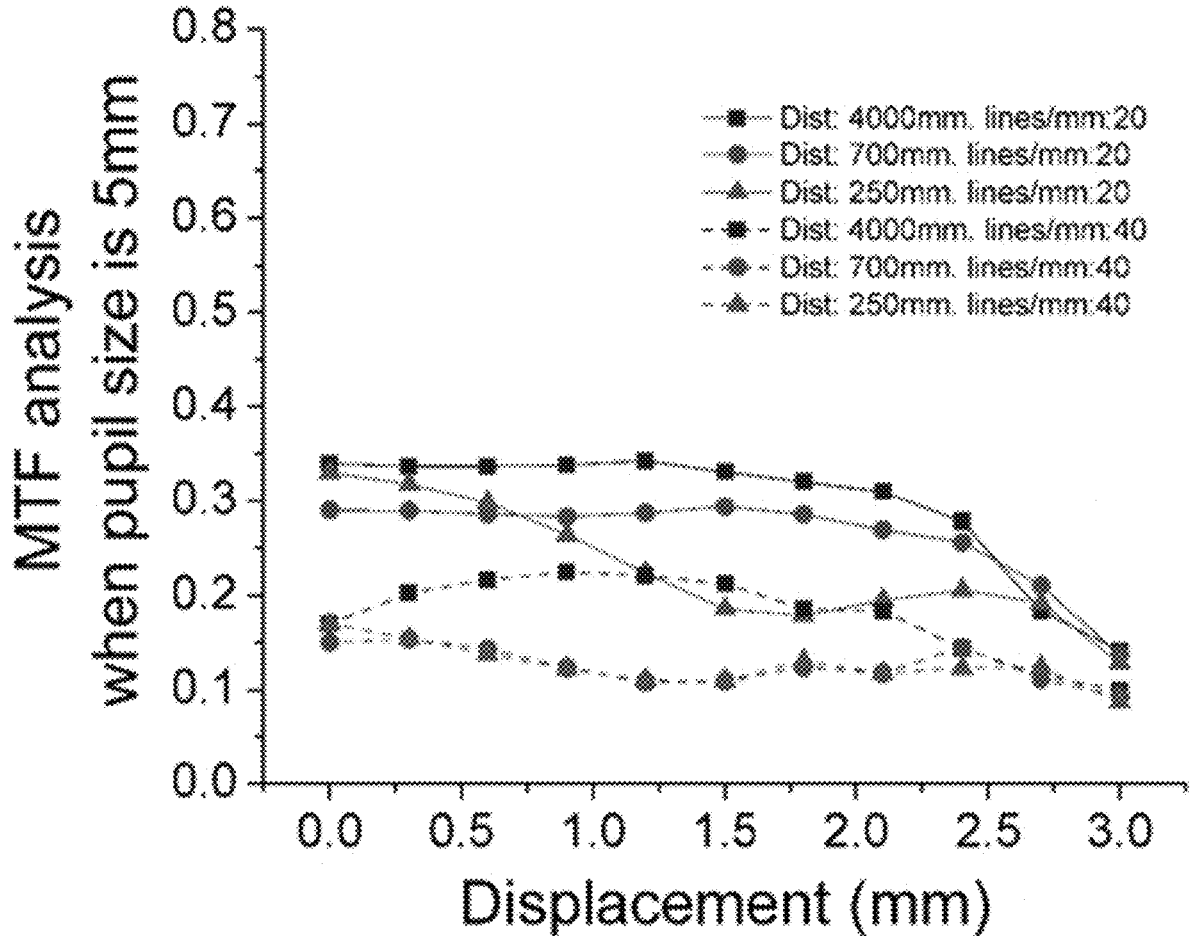

FIGS. 4A-4C show results from applying the general polynomial phase function in Eq. (9). The MTF and the corresponding image on the retina are shown for 4 m (FIG. 4A), 70 cm (FIG. 4B), and 40 cm (FIG. 4C) object distances. The pupil size is 5 mm. The MTF curves for different object distances are constant, and all the images for these object distances are similar and provide 20/20 vision.

The effects of large variation of the pupil size and the relatively large displacement of the contact/scleral lens with respect to the eye were carefully considered. For the design based on the general polynomial phase function, a summary of the results are plotted in FIGS. 5A-5D. As shown, excellent MTF values can be maintained even considering large pupil sizes and large displacement of the lens. It was found that the minimum MTF value that the eye can detect is about 0.02. The results demonstrate capability of techniques described herein, in accordance with various embodiments of the present disclosure, for correcting presbyopia with unprecedented DoF from 25 cm to infinity.

In some embodiments, asymmetric general polynomial phase functions or symmetric rational phase functions are utilized. The visual acuity at all distances may be no less than 20/25 and may be 20/20 in various implementations. Contrast sensitivity is not compromized for near vision, and the whole aperture of the contact lens is used for the natural binocular vision. These outcomes are superior to that of any existing presbyopia solution. A rotationally symmetric phase profile also allows the contact lens to be insensitive to the movement of the eye.

Certain techniques according to various embodiments of the present disclosure can make the vision insensitive to the object distance for a range from 25 cm to infinity, corresponding to a DoF of 4 D; therefore if the astigmatism is lower than 4 D, there will always be an axial position where the two focal points in the two meridians coincide. At this position, an image without astigmatism will be formed. Contact lenses with astigmatism correction can have much less relative movement with respect to the eye.

Embodiments of the present disclosure allow for an individualized contact/scleral lens design for each particular subject by using biometry parameters of each subject, for example using clinical measurement instruments. These biometry parameters can be entered into the optical design to optimize the coefficients of the polynomial terms. Notably, knowledge of the higher-order aberrations of each eye is not required, and no wavefront sensor is required for the process. The inherent aberrations can be automatically taken into account in the optimization procedure. The designs can also be extended to myopic and hyperopic eyes.

Using wavefront engineering techniques described herein, there can be a slight decrease in the image contrast. One alternative is to exploit the techniques for two contact lenses of the subject with different corrective power. By extending the DoF to a smaller range, the high contrast and natural binocular vision can be maintained. Further, the concepts can be applied to conventional monovision contact lenses.

The various embodiments described above are provided by way of illustration only and should not be construed to limit the scope of the present disclosure. Those skilled in the art will readily recognize that various modifications and changes may be made to the present disclosure without following the example embodiments and implementations illustrated and described herein, and without departing from the spirit and scope of the disclosure and claims here appended and those which may be filed in non-provisional patent application(s). Therefore, other modifications or embodiments as may be suggested by the teachings herein are particularly reserved.

Liquid Crystal Cell and Lens Doped with Nanoparticles for Enhanced Alignment

Some aspects of the present disclosure relate to liquid crystal apparatuses doped with nanoparticles to enhance alignment. Some example embodiments and implementations provide tunable optical lenses for vision correction, having a structure with doped nanoparticles in the liquid crystal portion and in one alignment layer.

Although example embodiments of the present disclosure are explained in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value. As used herein, "about" means within 20 percent or closer of a given value or range.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

As discussed herein, a "subject" may be any applicable human, animal, or other organism, and such references to a "subject" may relate particularly to vision components and functions of particular subject, for instance components and functions of and for eye(s) or portions thereof, or other optical/visual-related biological systems, tissues, fluids, etc. of the subject.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

The discussion of some example implementations also refers to corresponding results which includes experimental data. Experimental data presented herein is intended for the purposes of illustration and should not be construed as limiting the scope of the present disclosure in any way or excluding any alternative or additional embodiments.

FIG. 1 illustrates an apparatus that includes a liquid crystal layer ("NP-doped LC") doped with certain nanoparticles. The structure as shown also includes a top substrate that is comprised of a substantially transparent material such as glass or plastic. Below the top substrate is a first conductive layer ("electrode") comprised of a conductive material such as Indium Oxide, Tin oxide, or Indium Tin Oxide (ITO). Below the first conductive layer and above the liquid crystal layer is an alignment layer. The alignment layer can be configured to align the liquid crystal molecules of the liquid crystal layer in a predetermined orientation when no voltage is applied across the liquid crystal layer. For example, the alignment layer can be configured to cause the liquid crystal material to be in a homeotropic alignment state, wherein liquid crystal molecules are substantially perpendicular to the substrate when no voltage is applied across the liquid crystal layer. In some embodiments of the present disclosure, the alignment layer can be doped with certain nanoparticles, for example POSS (polyhedral oligomeric silsequioxanes) or gold, to enhance the desired alignment of the liquid crystal materials in the liquid crystal layer. For example, the nanoparticles can induce vertical alignment.

The liquid crystal layer is filled with liquid crystal materials such as positive or negative liquid crystal materials, and for example nematic liquid crystal material. In accordance with implementations and results described in further detail below, the inventor has shown that liquid crystals MLC 6608 and MLC 2059 with negative dielectric anisotropy show enhanced vertical alignment when the liquid crystal layer is doped with nanoparticles of POSS (polyhedral oligomeric silsequioxanes) or gold. When the liquid crystal layer is doped with such nanoparticles, rather than two or more alignment layers being required as in conventional approaches, only one alignment layer is needed for effective functionality. Among other benefits and advantages, eliminating the requirement for a second alignment layer is advantageous in that some alignment layers (e.g., polyimide) requires processing at high temperatures (e.g., 180° C.).

The lens structure of FIG. 6 also includes, below the liquid crystal layer, a second conductive layer ("electrode"). A "driver" can be connected to the first conductive layer and second conductive layer. The driver, via the conductive layers, can apply one or more voltages across the liquid crystal layer to induce changes in the properties of the liquid crystal such as changes of the alignment and/or orientation of the liquid crystal molecules. This thereby can change the optical properties of the overall structure to provide for vision correction of a subject. When provided in the setting of a lens, as will be described in further detail with respect to the apparatuses shown in FIGS. 9A and 9B, the applied voltage can be adjusted in order to control the refractive index of the liquid crystal layer and tune and/or adjust the focal length, optical power, etc. of the lens. Referring again to FIG. 6, a bottom substrate is disposed below the second conductive layer. The bottom substrate may be made of substantially transparent material such as glass or plastic.

Figure 7:
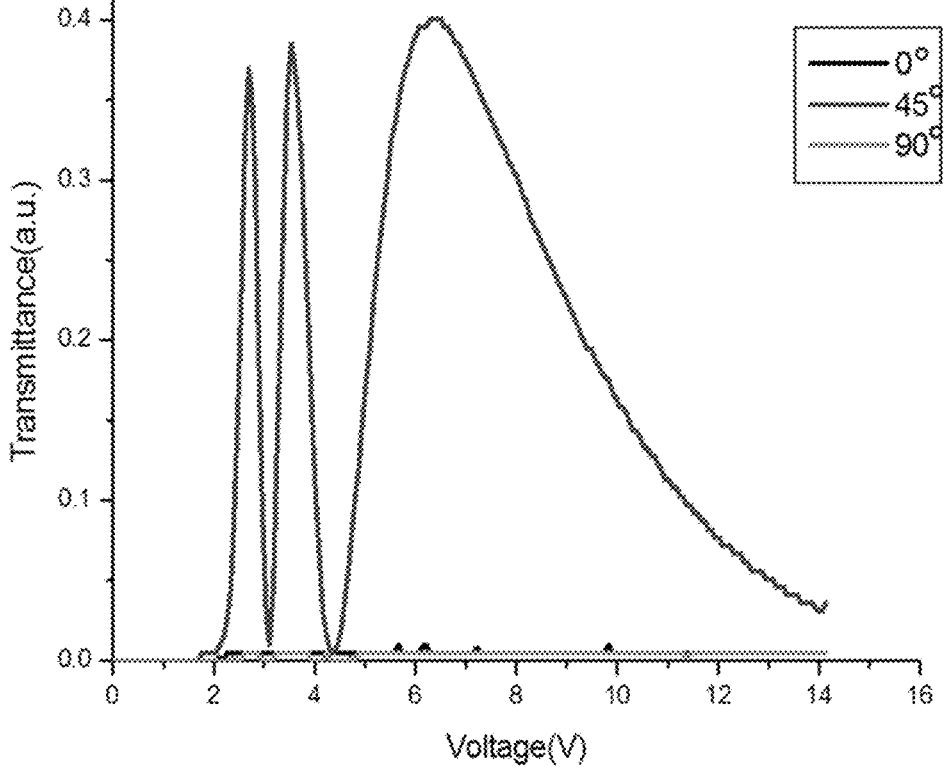
FIG. 7 shows a graph representation of phase modulation in an implementation of a liquid crystal layer doped with a first type of nanoparticles.
Figure 8:
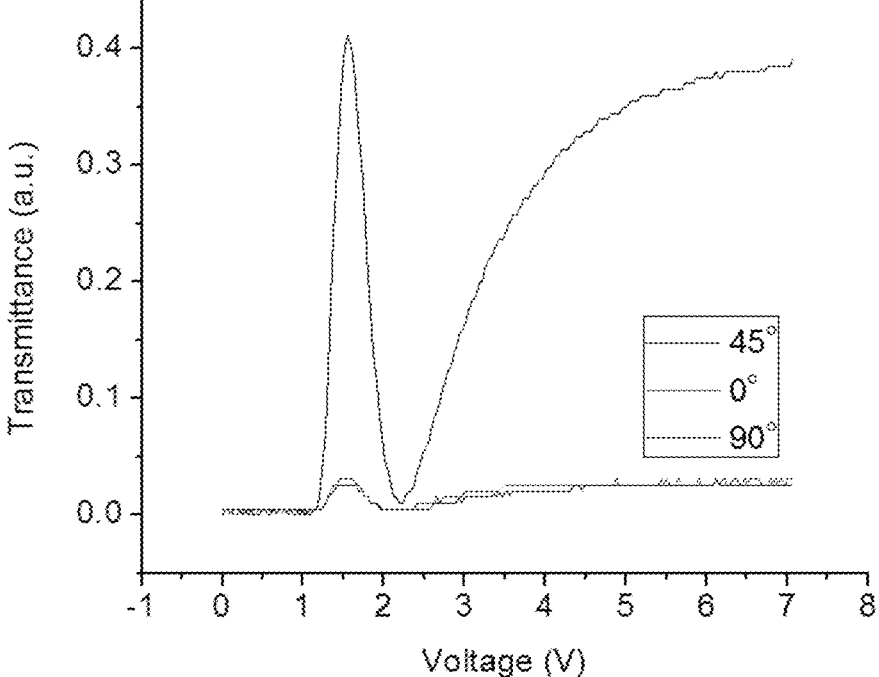
FIG. 8 shows a graph representation of phase modulation in an implementation of a liquid crystal layer doped with a second type of nanoparticles.

FIG. 7 shows a graph representation of transmittance versus voltage for a 1% concentration of POSS nanoparticles doped in MLC 2059. The inventor found that, for POSS nanoparticles, propyl-hepta-isobutyl substituted POSS and PSS-Octa(2-trichlorosilyethyl) substituted POSS provided good results, with a concentration of 0.5-1 wt % for propyl-hepta-isobutyl substituted POSS and a concentration of 1-2 wt % for PSS-Octa(2-trichlorosilyethyl). For purposes of a liquid crystal lens structure, MLC 2059 was found to provide higher birefringence than MLC 6608. These configurations with the above-mentioned materials and concentrations achieve reliable cell structures with excellent alignment of the liquid crystals and large tunability of refractive index. In some embodiments, the alignment layer is also doped with nanoparticles of POSS or gold, and it was found that vertical alignment of the liquid crystals is significantly enhanced with a doping concentration of more than 0.13 wt %. The inventor also found that in some implementations, gold nanoparticles can have better compatibility with the negative nematic liquid crystals. For example, FIG. 8 shows transmittance versus voltage for 5% gold nanoparticle-doped MLC 6608.

Figure 9A:
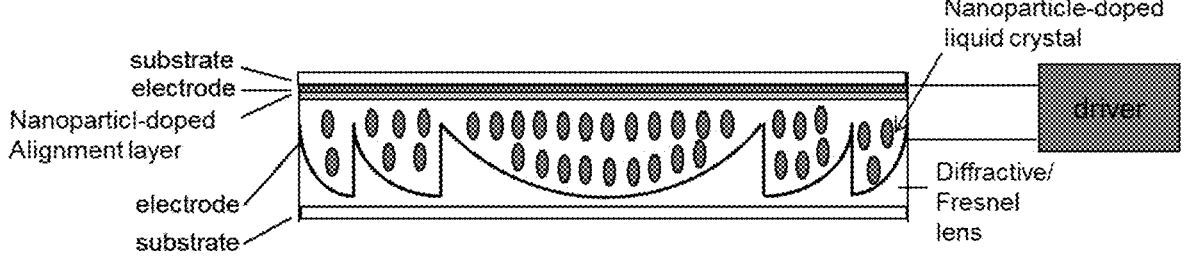
FIGS. 9A and 9B illustrate hybrid switchable liquid crystal lens apparatuses using a nanoparticle doped liquid crystal layer and nanoparticle-doped alignment layer, in accordance with some embodiments.
Figure 9B:
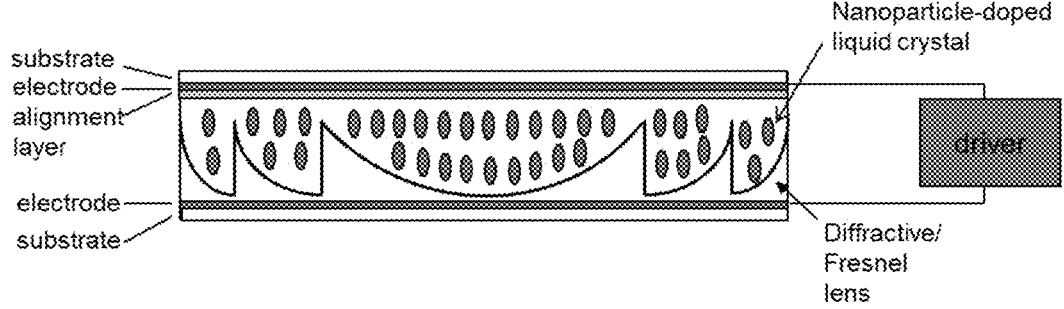

FIGS. 9A and 9B illustrate embodiments of hybrid switchable liquid crystal lens apparatuses that use a nanoparticle-doped liquid crystal layer and nanoparticle-doped alignment layer. The apparatus of FIG. 9A is comprised of a structure with a liquid crystal layer ("Nanoparticle-doped liquid crystal"), which may be comprised of the same or different liquid crystal materials as described above with respect to FIG. 6, that are doped with certain nanoparticles. A top substrate is comprised of a substantially transparent material such as glass or plastic, and below the top substrate is a first conductive layer ("electrode") comprised of a conductive material such as Indium Oxide, Tin oxide, or Indium Tin Oxide (ITO). Below the first conductive layer and above the liquid crystal layer is an alignment layer ("Nanoparticle-doped alignment layer"). The alignment layer can be configured to align the liquid crystal molecules of the liquid crystal layer in a predetermined direction when no voltage is applied across the liquid crystal layer. The alignment layer is doped with nanoparticles of POSS or gold (as described above with respect to the embodiments of FIGS. 6, 7, and 8), to enhance the desired alignment of the liquid crystal materials in the liquid crystal layer. For example, the nanoparticles can induce vertical alignment.

The lower portion of the apparatus of FIG. 9A includes a second substrate (e.g., substantially transparent and made of plastic) with a continuous groove phase profile which may be a continuous Fresnel lens phase profile or a continuous diffractive lens phase profile. The lens can be formed using a diamond turning technique and/or molding technique, for example. The first conductive layer (see "electrode" as labeled above "Nanoparticle-doped Alignment layer") and the second conductive layer (also labeled "electrode", disposed below the nanoparticle-doped alignment layer and running along the top surface of the lens) can be electrically connected to the driver, such that a voltage is applied across the liquid crystal layer such that the lens is continuously tunable. The applied voltage from the driver can be adjusted in order to control the refractive index of the liquid crystal layer and tune and/or adjust the focal length, optical power, etc. of the lens.

The apparatus of the embodiment shown in FIG. 9B shares many components and structure as the embodiment of FIG. 9A, including the top substrate, top conductive layer, nanoparticle-doped alignment layer and nanoparticle-doped liquid crystal layer, and the materials for these components can be the same as those described above for these similar components of FIG. 9A. The embodiment of FIG. 9B differs from that of FIG. 9A in that, as shown, a second conductive layer (electrode) is disposed below the grooved lens portion ("Diffractive/Fresnel lens") having the continuous grooved phase profile, and rather than the driver being electrically connected to a conductive layer along the top of the grooved lens portion as in FIG. 9A, a second conductive layer ("electrode") is disposed below the grooved lens portion and connected to the driver. The bottom substrate (below the bottom "electrode") can be substantially transparent material such as glass or plastic. Application of voltage by the driver, via the conductive layers, effects a change in the orientation of the liquid crystal molecules and thereby facilitates the active function of the structure as a corrective lens. The applied voltage from the driver can be adjusted in order to control the refractive index of the liquid crystal layer and tune and/or adjust the focal length, optical power, etc. of the lens.

Figure 6:
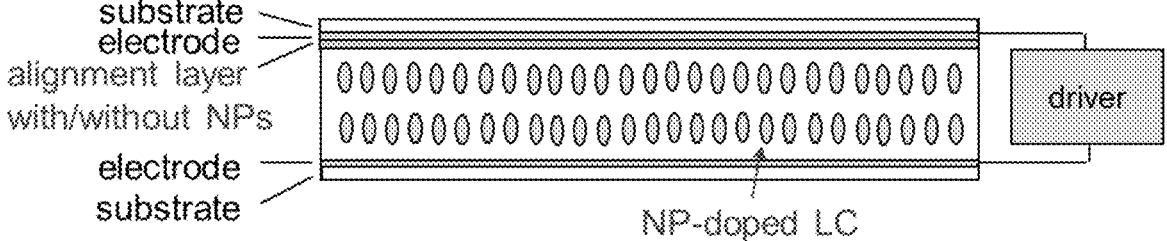
FIG. 6 illustrates an apparatus with a nanoparticle-doped liquid crystal layer, in accordance with one embodiment.

As discussed in some detail above with respect to the embodiment of FIG. 6, when the liquid crystal layer of the embodiments of FIGS. 9A and 9B is doped with the above-described nanoparticles and concentrations, only one alignment layer is needed for effective functionality, rather than the conventional approaches which require two or more alignment layers.

It should be noted that by using blue phase liquid crystal materials in this structure, no alignment layer is needed and the power of the lens can be adjusted by applying the voltages.

The various embodiments described above are provided by way of illustration only and should not be construed to limit the scope of the present disclosure. Those skilled in the art will readily recognize that various modifications and changes may be made to the present disclosure without following the example embodiments and implementations illustrated and described herein, and without departing from the spirit and scope of the disclosure and claims here appended and those which may be filed in non-provisional patent application(s). Therefore, other modifications or embodiments as may be suggested by the teachings herein are particularly reserved.

REFERENCE LIST

1. C. E. Letocha, The invention and early manufacture of bifocals, Survey of Ophthalmol. 35, 226 (1990).
2. T. Callina, T. P. Reynolds, Traditional methods for the treatment of presbyopia: spectacles, contact lenses, bifocal contact lenses, Ophthalmol. Clin. N. Am. 19, 25 (2006).

3. P. S. Soni, R. Patel, and R. S. Carlson, Is binocular contrast sensitivity at distance compromised with multifocal soft contact lenses used to correct presbyopia? Optom. Vis. Sci. 80, 505 (2003).
4. E. S. Bennett, Contact lens correction of presbyopia, Clin. Exp. Optom. 91, 265 (2008).
5. G. M. Morris and L. T. Nordan, Phakic intraocular lenses, Opt. Photon. News, 27 (September 2004).
6. M. Tomita, T. Kanamori, G. O. Waring, T. Nakamura, and S. Yukawa, Small-aperture corneal inlay implantation to treat presbyopia after laser in situ keratomileusis, J. Cataract Refract. Surg. 39, 898 (2013).
7. G. Li, D. L. Mathine, P. Valley, P. Ayras, J. Schwiegerling, B. Kippelen, S. Honkanen, and N. Peyghambarian, Switchable electro-optic diffractive lens with high efficiency for ophthalmic applications, Proc. Natl. Acad. Sci. USA 103, 6100 (2006).
8. G. Li, P. Valley, M. S. Giridhar, D. L. Mathine, G. Meredith, J. N. Haddock, B. Kippelen, and N. Peyghambarian, Large-aperture switchable thin diffractive lens with interleaved electrode pattern, Appl. Phys. Lett. 89, (October 2006).
9. G. Li, P. Valley, P. Ayras, S. Honkanen, and N. Peyghambarian, High-efficiency switchable flat diffractive ophthalmic lens with three-layer electrode pattern and two-layer via structures, Appl. Phys. Lett. 90, No. 10, 111105 (2007).
10. G. Li, D. Mathine, P. Valley, P. Ayras, J. Haddock, M. Giridhar, J. Schwiegerling, G. Meredith, B. Kippelen, S. Honkanen, N. Peyghambarian, Switchable Diffractive Lens for Vision Correction, Optics & Photonics News, "Optics in 2006", 28 (December 2006).
11. G. Li, US patent 2006/0164593 Adaptive electro-optic lens with variable focal length.
12. (Patent disclosure UA07-018) Switchable electro-optic lens for correction of both spherical and astigmatic refractive errors.
13. G. Li (invited), High-efficiency electro-optic diffractive lens, SPIE Symposium on Optics & Photonics, Conference 6310, Aug. 14, 2006, San Diego, CA
14. G. Li, (invited), Switchable electro-optic eyewear, SPIE Symposium on Optics & Photonics, Conference 6332, Aug. 13, 2006, San Diego, CA
15. G. Li (invited), Liquid crystal lenses for correction of presbyopia, Sixth International Workshop on Adaptive Optics in Industry and Medicine, Jun. 12-15, 2007, Galway, Ireland.
16. For example, J. Ruttimann, Nature, http://www.nature.com/news/2006/060403/full/060403-1.html#B1, Apr. 3, 2006.
17. Adrian Cho, Science, http://sciencenow.sciencemag.org/, Apr. 3, 2006.
18. D.Biello, Scientific American, http://www.sciam.com/article.cfm?chanID=sa003&articleID=00099837-91AB-1431-91AB83414B7F0000&ref=nature, Apr. 4, 2006.
19. G. Li, Adaptive lens, Progress in Optics 55, 199-283 (2010).
20. G. Li and T. Mauger, Adaptive lens for vision care and optical imaging, Frontiers in Optics, Optical Society of America, Rochester, October 2012. (Invited)
21. J. A. Futhey, Diffractive bifocal intraocular lens, Proc. SPIE 1052, 142 (1989).
22. G. Smith, D. A. Atchison, The eye and visual optical instruments, Cambridge University Press, 1997.

15 16

23. G. Vdovin, M. Loktev, A. Naumov, Opt. Express 11, 810 (2003).

24. A. W. Lohmann, Appl. Opt. 9, A new class of varifocal lenses, 1669 (1970) H. J. Caulfield, The Alvarez-Lohmann lens as a do-nothing machine," Opt. Laser Tech. 34, 1 (2002).

25. D.-Y. Zhang, V. Lien, Y. Berdichevsky, J. Choi, and Y.-H. Lo, Fluidic adaptive lens with high focal length tenability, Appl. Phys. Lett. 82, 3171 (2003).

26. http://evisionoptics.com/27.

27. http://glassescrafter.com/infromation/percentage-population-wears-glasses.html 28. Jane Cole, A closer look at presbyopia correction, Rev. of Optom. Feb. 15, 2016 https://www.reviewofoptomerty.com/atricle/a-closer-look-at-presbyopia-correction 29. A. S. Rajagopalan, E. S. Bennett, and V. Lakshaminarayanan, Visual performance of subjects wearing presbyopic contact lenses, Optometry and Vision Science 83, 611 (2006).

30. P. B. Morgan and N. Efron, Contact lens correction of presbyopia, Contact Lens & Anterior Eye 32, 191 (2009).

31. S. Kashani, A. A. Mearza, and C. Claoue, Refractive lens exchange for presbyopia, Contact Lens & Anterior Eye 31, 117 (2008).

32. J. Gispets, M. Arjona, J. Pujol, M. Vilaseca, G. Cardona, Task oriented visual satisfaction and wearing success with two different simultaneous vision multifocal soft contact lenses, J. Optometry 4, 76 (2011).

33. P. Gifford, T. Cannon, C. Lee, D. Lee, H. F. Lee, and H. A. Swarbrick, Ocular aberrations and visual function with multifocal versus single vision soft contact lenses, Contact Lens & Anterior Eye 36, 66 (2013).

34. S. Plainis, G. Ntzilepis, D. A. Atchison, and W. N. Charman, Through-focus performance with multifocal contact lenses: effect of binocularity, pupil diameter and inherent ocular aberrations, Ophthalmic & Physiological Opt. 33, 42 (2013).

35. W. T. Welford, "Use of annular apertures to increase focal depth," J. Opt. Soc. Am. 50, 749-753 (1960).

36. J. Campos, J. C. Escalera, C. J. R. Sheppard, M. J. Yzuel, "Axially invariant pupil filters," J. Mod. Optics 47, 57 (2000).

37. J. Ojeda-Castan̄ eda, E. Tepichin, and A. Diaz, "Arbitrary high focal depth with quasioptimum real and positive transmittance apodizer," Appl. Opt. 28, 2666-2670 (1989).

38. C. Fedtke, J. Sha, V. Thomas, K. Ehrmann, R. C. Bakaraju, Impact of Spherical Aberration Terms on Multifocal Contact Lens Performance, Optom. Vis. Sci. 94, 197 (2016).

39. D. Tilla, A. Munro, J. Chung, J. Sha, S. Delaney, D. Kho, V. Thomas, K. Ehrmann, R. C. Bakaraju, Short-term comparison between extended depth-of-focus prototype contact lenses and a commercially-available center-near multifocal, J. Optom. 10, 14 (2017).

40. R. C. Bakaraju, K. Ehrmann, A. Ho, Extended depth of focus contact lenses vs. two commercial multifocals: Part 1. Optical performance evaluation via computed through-focus retinal image quality metrics, J. Optom. (2017), http://dx.doi.org/10.1016/j.optom.2017.04.003.

41. R. C. Bakaraju, et al. Extended depth of focus contact lenses vs. two commercial multifocals: Part 2. Visual performance after 1 week of lens wear. J Optom. (2017), http://dx.doi.org/10.1016/j.optom.2017.04.001.

42. Z. Zalevsky, S. Ben Yaish, O. Yehezkel, and M. Belkin, "Thin spectacles for myopia, presbyopia and astigmatism insensitive vision," Opt. Express 15, 10790-10803 (2007).

43. A. Zlotnik, S. B. Yaish, O. Yehezkel, K. Lahav-Yacouel, M. Belkin, and Z. Zalevsky, Extended depth of focus contact lenses for presbyopia, Opt. Lett. 34, 2219 (2009).

44. T. Zhao and G. Li, Optimization for wavefront coded infinity microscope systems to extend depth of field, Biomedical Optics Express 4, 1464-1471 (2013).

45. Zemax 12 Optical design program user's manual, Radiant Zemax, 2012.

46. M. Liu, L. Dong, Y. Zhao, M. Hui and W. Jia, "Stationary phase analysis of generalized cubic phase mask wavefront coding," Opt. Communications 298-299, 67-74 (2013).

47. F. Zhou, G. Li, H. Zhang, and D. Wang, Rational phase mask to extend the depth of field in optical-digital hybrid imaging systems, Opt. Lett. 34, 380 (2009).

48. B. Watson and J. I. Yellott, A unified formula for light-adapted pupil size. J.Vision 12(10), 12 (2012).

What is claimed is:

1. A liquid crystal adaptive lens, comprising:
a liquid crystal layer, wherein the liquid crystal layer is doped with nanoparticles for enhancing alignment of nematic liquid crystal materials and the nanoparticles are comprised of polyhedral oligomeric silsesquioxanes (POSS) or gold in a concentration of 0.5-5.0 wt %;
a single alignment layer on top of a flat substrate, wherein the single alignment layer is a mixture of conventional alignment materials and the POSS or gold nanoparticles for enhancing alignment of the nematic liquid crystal materials in the liquid crystal layer, and the concentrations of the nanoparticles in the single alignment layer is 0.13-2.0 wt %; and
a lens portion, formed with a continuous groove phase profile of a diffractive or Fresnel lens, which is made of glass or plastic, coupled to the liquid crystal layer and configured such that, when a voltage is applied across the liquid crystal layer, one or more optical properties of the liquid crystal adaptive lens are changed to provide correction of vision for a subject.

2. The apparatus of claim 1, wherein there is no alignment layer on top of the surface of the lens portion.

3. The apparatus of claim 1, further comprising conductive layers disposed on a top and bottom of the liquid crystal layer and configured to receive the voltage and apply the voltage across the liquid crystal layer.

4. The apparatus of any one of claim 1, wherein one of the conductive layers is disposed on a top surface of the lens portion.

5. The apparatus of any one of claim 1, further comprising a voltage source configured to provide the voltage across the liquid crystal layer.

6. The apparatus of any one of claim 1, wherein the changes in the one or more optical properties when voltage is applied across the liquid crystal layer comprise changes in refractive index.

* * * * *